United States Patent [19]

Fikes et al.

[11] Patent Number: 5,750,395
[45] Date of Patent: May 12, 1998

[54] DNA ENCODING MAGE-1 C-TERMINAL CYTOTOXIC T LYMPHOCYTE IMMUNOGENIC PEPTIDES

[75] Inventors: John D. Fikes; Brian D. Livingston, both of San Diego; Alessandro D. Sette; John C. Sidney, both of La Jolla, all of Calif.

[73] Assignee: Cytel Corporation, San Diego, Calif.

[21] Appl. No.: 465,167

[22] Filed: Jun. 5, 1995

Related U.S. Application Data

[62] Division of Ser. No. 103,623, Aug. 6, 1993, abandoned.

[51] Int. Cl.$^6$ ............................. C12N 15/63; C12N 15/12
[52] U.S. Cl. ..................... 435/325; 435/69.3; 435/252.2; 435/252.3; 435/254.2; 435/320.1; 536/235
[58] Field of Search ......................... 435/69.3, 252.3, 435/320.1, 325, 254.2; 536/23.5

[56] References Cited

U.S. PATENT DOCUMENTS 5,342,774   8/1994   Boon et al. .
5,405,940   4/1995   Boon et al. .
5,462,871  10/1995   Boon-Falleur et al. .

OTHER PUBLICATIONS

Traversari, C. et al. Immunogenetics 35:142–152, Feb. 1992.
Bowie et al., "Deciphering the Message in Protein Sequences: Tolerance to Amino Acid Substitutions," *Science*, 247:1306–1310 (Mar. 16, 1990).
Herlyn and Koproski, "Melanoma Antigens: Immunological and Biological Characterization and Clinical Significance", *Ann. Rev. Immunol.* 6: 283–308 (1988).
Van den Eynde et al., "Presence on a human Melanoma of Multiple Antigens Recognized by Autologous CTL", *Int. J. Cancer* 44:634 (1989).
Deres, "In Vivo Priming of Virus–Specific Cytotoxic T Lymphocytes with Synthetic Lipopeptide Vaccine" *Nature* 342:561–564 (1989).
Kumar et al., "Amino Acid Variations at a Single Residue in an Autoimmune Peptide Profoundly Affect its Properties: T–cell Activation, Major Histocompatibility Complex Binding, and Ability to Block Experimental Allergic Encephalomyelitis," *Proc. Natl. Acad. Sci. USA*, 87:1337–1391 (1990).
Van Bleek et al., "Isolation of an Endogenously Processed Immunodominant Viral Peptide from the Class IH–2K$^b$ Molecule", *Nature* 348:213–216 (1990).
Rotzschke et al. "Isolation and Analysis of Naturally Processed Viral Peptides as Recognized by Cytotoxic T cells" *Nature* 348:252–254 (1990).
Schumacher et al., "Peptide Selection by MHC Class I Molecules", *Nature* 350:703–706 (1991).
Falk et al., "Allele–specific Motifs Revealed by Sequencing of Self–peptides Eluted from MHC Molecules", *Nature* 351:290–296 (1991).
Van der Bruggen et al., "A Gene Encoding an Antigen Recognized by Cytolytic T Lymphocytes on a Human Melanoma", *Science* 254: 1643–1647 (1991).
Traversari et al., "A Nonapeptide Encoded by Human Gene MAGE–1 is Recognized on HLA–A1 by Cytolytic T Lymphocytes Directed Against Tumor Antigen MZ2–E", *J. Exp. Med.* 176: 1453–1457 (1992).
Paul, ed. *Fundamental Immunology*, 3d., Raven Press, NY, pp. 977–978, 1222–1223 (1993).
Lanzavecchia, "Identifying Strategies for Immune Intervention," *Science*, 260:937–943 (1993).
Cohen, "Cancer Vaccines Get a Shot in the Arm," *Science*, 262:841–843 (1993).

*Primary Examiner*—Anthony C. Caputa
*Attorney, Agent, or Firm*—Townsend and Townsend and Crew

[57] ABSTRACT

The complete nucleotide and amino acid sequences of the human MAGE-1 antigen are provided. Peptides from residues of the C-terminal are used to define epitopes that stimulate HLA-restricted cytotoxic T lymphocyte activity against MAGE-1 antigens. The peptides are particularly useful in methods for stimulating the immune response of individuals against MAGE-1 antigens associated with melanomas.

3 Claims, 8 Drawing Sheets

FIG. 1A

SEQUENCE RANGE: 1 TO 2420

```
        10         20         30         40         50         60
         *          *          *          *          *          *
GGATC CAGGC CCTGC CAGGA AAAAT ATAAG GGCCC TGCGT GAGAA CAGAG GGGGT CATCC
        70         80         90        100        110        120
         *          *          *          *          *          *
ACTGC ATCAG AGTGG GGATG TCACA GAGTC CAGCC CACCC TCCTG GTAGC ACTGA GAAGC
       130        140        150        160        170        180
         *          *          *          *          *          *
CAGGG CTGTG CTTGC GGTCT GCACC CTGAG GGCCC GTGGA TTCCT CTTCC TGGAG CTCCA
       190        200        210        220        230        240
         *          *          *          *          *          *
GGAAC CAGGC AGTGA GGCCT TGGTC TGAGA CAGTA TCCTC AGGTC ACAGA GCAGA GGATG
       250        260        270        280        290        300
         *          *          *          *          *          *
CACAG GGTGT GCCAG CAGTG AATGT TTGCC CTGAA TGCAC ACCAA GGGCC CCACC TGCCA
       310        320        330        340        350        360
         *          *          *          *          *          *
CAGGA CACAT AGGAC TCCAC AGAGT CTGGC CTCAC CTCCC TACTG TCAGT CCTGT AGAAT
       370        380        390        400        410        420
         *          *          *          *          *          *
CGACC TCTGC TGGCC GGCTG TACCC TGAGT ACCCT CTCAC TTCCT CCTTC AGGTT TTCAG
       430        440        450        460        470        480
         *          *          *          *          *          *
GGGAC AGGCC AACCC AGAGG ACAGG ATTCC CTGGA GGCCA CAGAG GAGCA CCAAG GAGAA
```

FIG. 1B

```
                     490         500         510         520         530         540
                      *           *           *           *           *           *
            GATCT GTAAG TAGGC CTTTG TTAGA GTCTC CAAGG TTCAG TTCTC AGCTG AGGCC TCTCA
                     550         560         570         580         590         600
                      *           *           *           *           *           *
            CACAC TCCCT CTCTC CCCAG GCCTG TGGGT CTTCA TTGCC CAGCT CCTGC CCACA CTCCT
                     610         620         630         640         650
                      *           *           *           *           *
            GCCTG CTGCC CTGAC GAGAG TCATC ATG TCT CTT GAG CAG AGG AGT CTG CAC TGC
                                               Met Ser Leu Glu Gln Arg Ser Leu His Cys>
                660         670         680         690         700
                 *           *           *           *           *
            AAG CCT GAG GAA GCC CTT GAG GCC CAA GAG CAA GAG GCC CTG GGC CTG CTG GTG
            Lys Pro Glu Glu Ala Leu Glu Ala Gln Glu Gln Glu Ala Leu Gly Leu Leu Val
            710         720         730         740         750         760
             *           *           *           *           *           *
            CAG GCT GCC ACC TCC TCC TCT CCT CTG GTC CTG GGC ACC CTG GAG GAG GTG
            Gln Ala Ala Thr Ser Ser Ser Pro Leu Val Leu Gly Thr Leu Glu Glu Val>
                770         780         790         800         810
                 *           *           *           *           *
            CCC ACT GCT GGG TCA ACA GAT CCT CAG AGT CCT CAG GGA GCC TCC GCC TTT
            Pro Thr Ala Gly Ser Thr Asp Pro Gln Ser Pro Gln Gly Ala Ser Ala Phe>
            820         830         840         850         860         870
             *           *           *           *           *           *
            CCC ACT ACC ATC AAC TTC ACT CGA CAG AGG CAA CCC AGT GAG GGT TCC AGC AGC
            Pro Thr Thr Ile Asn Phe Thr Arg Gln Arg Gln Pro Ser Glu Gly Ser Ser Ser>
```

FIG. 1C

```
        880         890         900         910         920
         *           *           *           *           *
CGT GAA GAG GAG GGG CCA AGC ACC TCT ATC CTG GAG TCC TTC CGA GCA
Arg Glu Glu Glu Gly Pro Ser Thr Ser Ile Leu Glu Ser Leu Phe Arg Ala>
        930         940         950         960         970
         *           *           *           *           *
GTA ATC ACT AAG AAG GTG GCT GAT TTG GTT GGT TTT CTG CTC CTC AAA TAT CGA
Val Ile Thr Lys Lys Val Ala Asp Leu Val Gly Phe Leu Leu Leu Lys Tyr Arg>
980         990        1000        1010        1020        1030
 *           *           *           *           *           *
GCC AGG GAG CTG TGT CCA GTC ACA AAG GCA GAA ATG CTG GAG AGT GTC ATC AAA AAT TAC
Ala Arg Glu Leu Cys Pro Val Thr Lys Ala Glu Met Leu Glu Ser Val Ile Lys Asn Tyr>
        1040        1050        1060        1070        1080
         *           *           *           *           *
AAG CAC TGT TTT CCT GAG ATC TTC GGC AAA GCC TCT GAG TCC TTG CAG CTG GTC
Lys His Cys Phe Pro Glu Ile Phe Gly Lys Ala Ser Glu Ser Leu Gln Leu Val>
1090        1100        1110        1120        1130        1140
 *           *           *           *           *           *
TTT GGC ATT GAC GTG AAG GAA GCA GAC CCC ACC GGC CAC TCC TAT GTC CTT GTC
Phe Gly Ile Asp Val Lys Glu Ala Asp Pro Thr Gly His Ser Tyr Val Leu Val>
        1150        1160        1170        1180        1190
         *           *           *           *           *
ACC TGC CTA GGT CTC TCC TAT GAT GGC CTG CTG GGT GAT AAT CAG ATC ATG CCC
Thr Cys Leu Gly Leu Ser Tyr Asp Gly Leu Leu Gly Asp Asn Gln Ile Met Pro>
1200        1210        1220        1230        1240
 *           *           *           *           *
AAG ACA GGC TTC CTG ATA ATT GTC CTG ATT GCA ATG GAG GGC CAT
Lys Thr Gly Phe Leu Ile Ile Val Leu Val Met Ile Ala Met Glu Gly His>
```

FIG. 1D

```
1250
   *       1260        1270        1280        1290        1300
GCT CCT GAG GAG GAA ATC TGG GAG GAG CTG AGT GTG ATG GAG GTG TAT GAT GGG
Ala Pro Glu Glu Glu Ile Trp Glu Glu Leu Ser Val Met Glu Val Tyr Asp Gly>
       1310        1320        1330        1340        1350
            *           *           *           *           *
AGC GAG CAC AGT GCC TAT GGG GAG TAC CGG AAG AAG CTG ACC CAA GAT TTG GTG
Arg Glu His Ser Ala Tyr Gly Glu Tyr Arg Lys Leu Thr Gln Asp Leu Val>
1360        1370        1380        1390        1400        1410
   *           *           *           *           *           *
CAG GAA AAG TAC CTG TAT CTG GAG TAC CGG CAG CCC GAC AGT GAT CCC GCA CGC TAT
Gln Glu Lys Tyr Leu Tyr Leu Glu Tyr Arg Gln Pro Asp Ser Asp Pro Ala Arg Tyr>
       1420        1430        1440        1450        1460
            *           *           *           *           *
GAG TTC CTG TGG GGT CCA AGG GCC CTC GCT GAA ACC AGC TAT GTG AAA GTC CTT
Glu Phe Leu Trp Gly Pro Arg Ala Leu Ala Glu Thr Ser Tyr Val Lys Val Leu>
1470        1480        1490        1500        1510
   *           *           *           *           *
GAG TAT GTG ATC AAG GTC AGT GCA AGA GTT CGC TTT TTC TTC CCA TCC CTG CGT
Glu Tyr Val Ile Lys Val Ser Ala Arg Val Arg Phe Phe Phe Pro Ser Leu Arg>
1520        1530        1540        1550        1560        1570
   *           *           *           *           *           *
GAA GCA GCT TTG AGA GAG GAA GAG GGA GTC TGA GCATG AGTTG CAGCC AAGGC
Glu Ala Ala Leu Arg Glu Glu Glu Gly Val>
1580        1590        1600        1610        1620        1630
   *           *           *           *           *           *
CAGTG GGAGG GGGAC TGGGC CAGTG CACCT TCCAG GGCCG CGTCC AGCAG CTTCC CCTGC
```

FIG. 1E

```
     1640       1650       1660       1670       1680       1690
       *          *          *          *          *          *
CTCGT GTGAC ATGAG GCCCA TTCTT CACTC TGAAG AGAGC GGTCA GTGTT CTCAG TAGTA
     1700       1710       1720       1730       1740       1750
       *          *          *          *          *          *
GGTTT CTGTT CTATT GGGTG ACTTG GAGAT TTATC TTTGT TCTCT TTTGG AATTG TTCAA
     1760       1770       1780       1790       1800       1810
       *          *          *          *          *          *
ATGTT TTTTT TTAAG GGATG GTTGA ATGAA CTTCA GCATC CAAGT TTATG AATGA CAGCA
     1820       1830       1840       1850       1860       1870
       *          *          *          *          *          *
GTCAC ACAGT TCTGT GTATA TAGTT TAAGG GTAAG AGTCT TGTGT TTTAT TCAGA TTGGG
     1880       1890       1900       1910       1920       1930
       *          *          *          *          *          *
AAATC CATTC TATTT TGTGA ATTGG GATAA TAACA GCAGT GGAAT AAGTA CTTAG AAATG
     1940       1950       1960       1970       1980       1990
       *          *          *          *          *          *
TGAAA AATGA GCAGT AAAAT AGATG AGATA AAGAA CTAAA GAAAT TAAGA GATAG TCAAT
     2000       2010       2020       2030       2040       2050
       *          *          *          *          *          *
TCTTG CCTTA TACCT CAGTC TATTC TGTAA AATTT TTAAA GATAT ATGCA TACCT GGATT
     2060       2070       2080       2090       2100       2110
       *          *          *          *          *          *
TCCTT GGCTT CTTTG AGAAT GTAAG AGAAA TTAAA TCTGA ATAAA GAATT CTTCC TGTTC
     2120       2130       2140       2150       2160       2170
       *          *          *          *          *          *
ACTGG CTCTT TTCTT CTCCA TGCAC TGAGC ATCTG CTTTT TGGAA GGCCC TGGGT TAGTA
     2180       2190       2200       2210       2220       2230
       *          *          *          *          *          *
GTGGA GATGC TAAGG TAAGC CAGAC TCATA CCCAC CCATA GGGTC GTAGA GTCTA GGAGC
```

FIG. 1F

```
      2240       2250       2260       2270       2280       2290
        *          *          *          *          *          *
TGCAG TCACG TAATC GAGGT GGCAA GATGT CCTCT AAAGA TGTAG GGAAA AGTGA GAGAG
      2300       2310       2320       2330       2340       2350
        *          *          *          *          *          *
GGGTG AGGGT GTGGG GCTCC GGGTG AGAGT GGTGG AGTGT CAATG CCCTG AGCTG GGGCA
      2360       2370       2380       2390       2400       2410
        *          *          *          *          *          *
TTTTG GGCTT TGGGA AACTC CAGTT CCTTC TGGGC GAGCT GATTG TAATG ATCTT GGGTG
      2420
        *
GATCC
```

FIG. 2

```
GB  MSLEQRSLHCKPEEALEAQQEALGLVCVQAATSSSSPLVLGTLEEVPTAGSTDPPQSPQGASAFPTTINFTRQRQPSEGSSS
    REEEGPSTSCILESLFRAVITKKVADLVGFLLLKYRAREPVTKAEMLESVIKNYKHCFPEIFGKASESLQLVFGIDVKEADP
                                                                  H A M   S S C
    TGHSYVLVTCLGLSYDGLLGDNQIMPKTGFLIIVLVMIAMEGGHAPEEIWEELSVMEVYDGREHSAYGEPRKLLTQDLV
                                                                CAC GCT ATG AGT TCC TGT
                                                                 H   A   M   S   S   C
GB        Q   E   K   Y   L   E   Y   G   R   C   R   T   V   I   P   H   A   M   S   S   C
    CAG GAA AAG TAC CTG GAG TAC -GGC AGG TGC CGG ACA GTG ATC CCG CAC GCT ATG AGT TCC TGT
    CAG GAA AAG TAC CTG GAG TAC     GAG TAC CGG CAG GTG CCG GAC AGT GAT CCC GCA CGC TAT GAG TTC CTG
CY   Q   E   K   Y   L   E   Y       E   Y   R   Q   V   P   D   S   D   P   A   R   Y   E   F   L

GB  G V Q G P S L K P A M *
CY  W G P R A L A E T S Y V K V L E Y V I K V S A R V R F F F P S L R E A A L R E E E G V
```

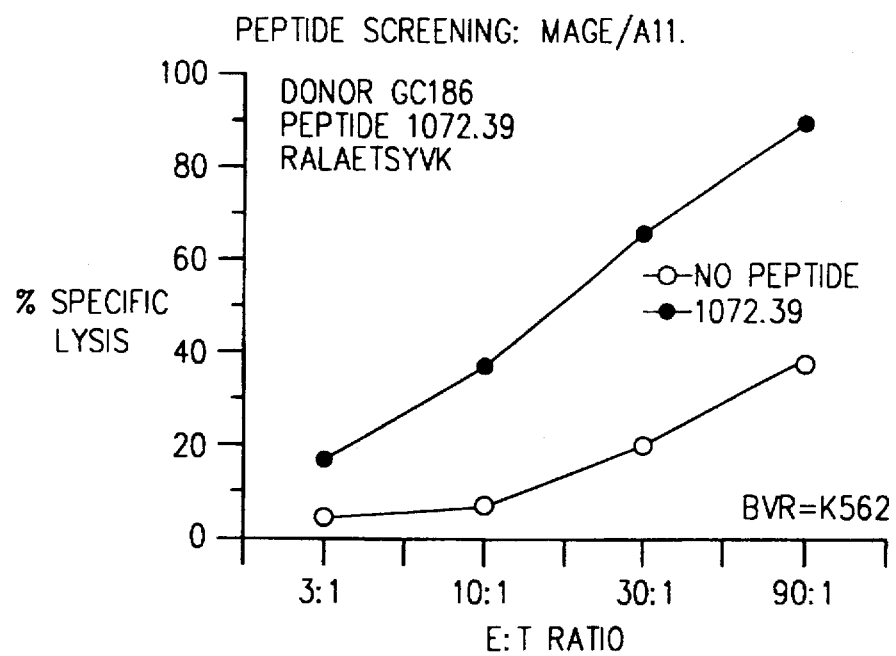

14

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:1:

```
Arg Gln Val Pro Asp Ser Asp Pro Ala Arg Tyr Glu Phe Leu Trp Gly
  1               5                  10                  15

Pro Arg Ala Leu Ala Glu Thr Ser Tyr Val Lys Val Leu Glu Tyr Val
               20                  25                  30

Ile Lys Val Ser Ala Arg Val Arg Phe Phe Phe Pro Ser Leu Arg Glu
           35                  40                  45

Ala Ala Leu Arg Glu Glu Glu Glu Gly Val
       50                  55
```

( 2 ) INFORMATION FOR SEQ ID NO:2:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:2:

```
Glu Thr Ser Tyr Val Lys Val Leu Glu Tyr
  1               5                  10
```

( 2 ) INFORMATION FOR SEQ ID NO:3:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:3:

```
Thr Ser Tyr Val Lys Val Leu Glu Tyr
  1               5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Lys Val Leu Glu Tyr Val Ile Lys Val
1               5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Phe Leu Trp Gly Pro Arg Ala Leu Ala
1               5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Ala Leu Arg Glu Glu Glu Glu Gly Val
1               5
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Ala Leu Ala Glu Thr Ser Tyr Val Lys Val
1               5                   10
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Tyr Val Ile Lys Val Ser Ala Arg Val
1               5
```

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Arg Ala Leu Ala Glu Thr Ser Tyr Val Lys Val
1               5                   10
```

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Val Pro Asp Ser Asp Pro Ala Arg Tyr
1               5
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Arg Val Arg Phe Phe Phe Pro Ser Leu Arg
1               5                   10
```

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Ala Leu Ala Glu Thr Ser Tyr Val Lys Val Lys
1               5                   10
```

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Arg Ala Leu Ala Glu Thr Ser Tyr Val Lys Val Lys
1               5                   10
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Asp  Leu  Val  Gln  Glu  Lys  Tyr  Leu  Glu  Tyr
 1                  5                        10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Tyr  Val  Ile  Lys  Val  Ser  Ala  Arg  Val  Arg
 1                  5                        10
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Leu  Val  Gln  Glu  Lys  Tyr  Leu  Glu  Tyr
 1                  5
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

```
Ser  Tyr  Val  Lys  Val  Leu  Glu  Tyr  Val  Ile
 1                  5                        10
```

( 2 ) INFORMATION FOR SEQ ID NO:18:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
Gln  Tyr  Ile  Lys  Ala  Asn  Ser  Lys  Phe  Ile  Gly  Ile  Thr  Glu
 1                  5                        10
```

( 2 ) INFORMATION FOR SEQ ID NO:19:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Lys  Ile  Ala  Lys  Met  Lys  Ala  Ser  Ser  Val  Phe  Asn  Val  Val  Asn  Ser
 1                   5                        10                       15
```

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Asp  Ile  Glu  Lys  Lys  Ile  Ala  Lys  Met  Lys  Ala  Ser  Ser  Val  Phe  Asn
 1                   5                        10                       15
Val  Val  Asn  Ser
                 20
```

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Ile  Ser  Gln  Ala  Val  His  Ala  Ala  His  Ala  Glu  Ile  Asn  Glu
 1                   5                        10
```

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

```
Pro  Lys  Tyr  Val  Lys  Gln  Asn  Thr  Leu  Lys  Leu  Ala  Thr
 1                   5                        10
```

( 2 ) INFORMATION FOR SEQ ID NO:23:

( i ) SEQUENCE CHARACTERISTICS:
        ( A ) LENGTH: 2420 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS ( B ) LOCATION: 626..1552

( x i ) SEQUENCE DESCRIPTION: SEQ ID NO:23:

| | | | | | |
|---|---|---|---|---|---|
| GGATCCAGGC | CCTGCCAGGA | AAAATATAAG | GGCCCTGCGT | GAGAACAGAG | GGGGTCATCC | 60 |
| ACTGCATGAG | AGTGGGGATG | TCACAGAGTC | CAGCCCACCC | TCCTGGTAGC | ACTGAGAAGC | 120 |
| CAGGGCTGTG | CTTGCGGTCT | GCACCCTGAG | GGCCCGTGGA | TTCCTCTTCC | TGGAGCTCCA | 180 |
| GGAACCAGGC | AGTGAGGCCT | TGGTCTGAGA | CAGTATCCTC | AGGTCACAGA | GCAGAGGATG | 240 |
| CACAGGGTGT | GCCAGCAGTG | AATGTTTGCC | CTGAATGCAC | ACCAAGGGCC | CCACCTGCCA | 300 |
| CAGGACACAT | AGGACTCCAC | AGAGTCTGGC | CTCACCTCCC | TACTGTCAGT | CCTGTAGAAT | 360 |
| CGACCTCTGC | TGGCCGGCTG | TACCCTGAGT | ACCCTCTCAC | TTCCTCCTTC | AGGTTTTCAG | 420 |
| GGACAGGCC | AACCCAGAGG | ACAGGATTCC | CTGGAGGCCA | CAGAGGAGCA | CCAAGGAGAA | 480 |
| GATCTGTAAG | TAGGCCTTTG | TTAGAGTCTC | CAAGGTTCAG | TTCTCAGCTG | AGGCCTCTCA | 540 |
| CACACTCCCT | CTCTCCCAG | GCCTGTGGGT | CTTCATTGCC | CAGCTCCTGC | CCACACTCCT | 600 |
| GCCTGCTGCC | CTGACGAGAG | TCATCATGTC | TCTTGAGCAG | AGGAGTCTGC | ACTGCAAGCC | 660 |
| TGAGGAAGCC | CTTGAGGCCC | AACAAGAGGC | CCTGGGCCTG | GTGTGTGTGC | AGGCTGCCAC | 720 |
| CTCCTCCTCC | TCTCCTCTGG | TCCTGGGCAC | CCTGGAGGAG | GTGCCCACTG | CTGGGTCAAC | 780 |
| AGATCCTCCC | CAGAGTCCTC | AGGGAGCCTC | CGCCTTTCCC | ACTACCATCA | ACTTCACTCG | 840 |
| ACAGAGGCAA | CCCAGTGAGG | GTTCCAGCAG | CCGTGAAGAG | GAGGGGCCAA | GCACCTCTTG | 900 |
| TATCCTGGAG | TCCTTGTTCC | GAGCAGTAAT | CACTAAGAAG | GTGGCTGATT | TGGTTGGTTT | 960 |
| TCTGCTCCTC | AAATATCGAG | CCAGGGAGCC | AGTCACAAAG | GCAGAAATGC | TGGAGAGTGT | 1020 |
| CATCAAAAAT | TACAAGCACT | GTTTTCCTGA | GATCTTCGGC | AAAGCCTCTG | AGTCCTTGCA | 1080 |
| GCTGGTCTTT | GGCATTGACG | TGAAGGAAGC | AGACCCCACC | GGCCACTCCT | ATGTCCTTGT | 1140 |
| CACCTGCCTA | GGTCTCTCCT | ATGATGGCCT | GCTGGGTGAT | AATCAGATCA | TGCCCAAGAC | 1200 |
| AGGCTTCCTG | ATAATTGTCC | TGGTCATGAT | TGCAATGGAG | GGCGGCCATG | CTCCTGAGGA | 1260 |
| GGAAATCTGG | GAGGAGCTGA | GTGTGATGGA | GGTGTATGAT | GGGAGGGAGC | ACAGTGCCTA | 1320 |
| TGGGGAGCCC | AGGAAGCTGC | TCACCCAAGA | TTTGGTGCAG | GAAAAGTACC | TGGAGTACCG | 1380 |
| GCAGGTGCCG | GACAGTGATC | CCGCACGCTA | TGAGTTCCTG | TGGGGTCCAA | GGGCCCTCGC | 1440 |
| TGAAACCAGC | TATGTGAAAG | TCCTTGAGTA | TGTGATCAAG | GTCAGTGCAA | GAGTTCGCTT | 1500 |
| TTTCTTCCCA | TCCCTGCGTG | AAGCAGCTTT | GAGAGAGGAG | GAAGAGGGAG | TCTGAGCATG | 1560 |
| AGTTGCAGCC | AAGGCCAGTG | GGAGGGGGAC | TGGGCCAGTG | CACCTTCCAG | GGCCGCGTCC | 1620 |
| AGCAGCTTCC | CCTGCCTCGT | GTGACATGAG | GCCCATTCTT | CACTCTGAAG | AGAGCGGTCA | 1680 |
| GTGTTCTCAG | TAGTAGGTTT | CTGTTCTATT | GGGTGACTTG | GAGATTTATC | TTTGTTCTCT | 1740 |
| TTTGGAATTG | TTCAAATGTT | TTTTTTAAG | GGATGGTTGA | ATGAACTTCA | GCATCCAAGT | 1800 |
| TTATGAATGA | CAGCAGTCAC | ACAGTTCTGT | GTATATAGTT | TAAGGGTAAG | AGTCTTGTGT | 1860 |
| TTTATTCAGA | TTGGGAAATC | CATTCTATTT | TGTGAATTGG | GATAATAACA | GCAGTGGAAT | 1920 |
| AAGTACTTAG | AAATGTGAAA | AATGAGCAGT | AAAATAGATG | AGATAAAGAA | CTAAAGAAAT | 1980 |
| TAAGAGATAG | TCAATTCTTG | CCTTATACCT | CAGTCTATTC | TGTAAAATTT | TTAAAGATAT | 2040 |
| ATGCATACCT | GGATTTCCTT | GGCTTCTTTG | AGAATGTAAG | AGAAATTAAA | TCTGAATAAA | 2100 |
| GAATTCTTCC | TGTTCACTGG | CTCTTTTCTT | CTCCATGCAC | TGAGCATCTG | CTTTTTGGAA | 2160 |
| GGCCCTGGGT | TAGTAGTGGA | GATGCTAAGG | TAAGCCAGAC | TCATACCCAC | CCATAGGGTC | 2220 |
| GTAGAGTCTA | GGAGCTGCAG | TCACGTAATC | GAGGTGGCAA | GATGTCCTCT | AAAGATGTAG | 2280 |

```
GGAAAAGTGA GAGAGGGGTG AGGGTGTGGG GCTCCGGGTG AGAGTGGTGG AGTGTCAATG      2340

CCCTGAGCTG GGGCATTTTG GGCTTTGGGA AACTGCAGTT CCTTCTGGGG GAGCTGATTG      2400

TAATGATCTT GGGTGGATCC                                                  2420
```

( 2 ) INFORMATION FOR SEQ ID NO:24:

( i ) SEQUENCE CHARACTERISTICS:
        ( A ) LENGTH: 309 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

```
Met Ser Leu Glu Gln Arg Ser Leu His Cys Lys Pro Glu Glu Ala Leu
 1               5                  10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305
```

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Pro Arg Ala Leu Ala Glu Thr Ser Tyr
1                   5
```

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

```
Tyr Val Lys Val Leu Glu Tyr Val Ile
1                   5
```

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

```
Tyr Val Ile Lys Val Ser Ala Arg Val
1                   5
```

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

```
Arg Ala Leu Ala Glu Thr Ser Tyr Val
1                   5
```

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Leu Ala Glu Thr Ser Tyr Val Lys Val
1                   5
```

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Gln Val Pro Asp Ser Asp Pro Ala Arg
    1                   5

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Lys Val Ser Ala Arg Val Arg Phe Phe
    1                   5

(2) INFORMATION FOR SEQ ID NO:32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Ala Leu Ala Glu Thr Ser Tyr Val Lys
    1                   5

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Val Ile Lys Val Ser Ala Arg Val Arg
    1                   5

(2) INFORMATION FOR SEQ ID NO:34:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Pro Ser Leu Arg Glu Ala Ala Leu Arg
    1                   5

( 2 ) INFORMATION FOR SEQ ID NO:35:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

```
Asp Ser Asp Pro Ala Arg Tyr Glu Phe
1               5
```

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Val Ser Ala Arg Val Arg Phe Phe Phe
1               5
```

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

```
Val Gln Glu Lys Tyr Leu Glu Tyr Arg
1               5
```

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

```
Glu Phe Leu Trp Gly Pro Arg Ala Leu
1               5
```

( 2 ) INFORMATION FOR SEQ ID NO:39:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:39:

```
Val Leu Glu Tyr Val Ile Lys Val Ser Ala
1               5                   10
```

( 2 ) INFORMATION FOR SEQ ID NO:40:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

```
Leu Ala Glu Thr Ser Tyr Val Lys Val Leu
1               5                   10
```

( 2 ) INFORMATION FOR SEQ ID NO:41:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:41:

```
Ala Ala Leu Arg Glu Glu Glu Glu Gly Val
1               5                   10
```

( 2 ) INFORMATION FOR SEQ ID NO:42:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:42:

```
Tyr Val Lys Val Leu Glu Tyr Val Ile Lys
1               5                   10
```

( 2 ) INFORMATION FOR SEQ ID NO:43:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:43:

```
Leu Val Gln Glu Lys Tyr Leu Glu Tyr Arg
1               5                   10
```

( 2 ) INFORMATION FOR SEQ ID NO:44:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

```
Arg Val Arg Phe Phe Phe Pro Ser Leu Arg
1               5                   10
```

( 2 ) INFORMATION FOR SEQ ID NO:45:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:45:

```
Gln  Val  Pro  Asp  Ser  Asp  Pro  Ala  Arg  Tyr
1                   5                        10
```

( 2 ) INFORMATION FOR SEQ ID NO:46:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:46:

```
Lys  Val  Ser  Ala  Arg  Val  Arg  Phe  Phe  Phe
1                   5                        10
```

( 2 ) INFORMATION FOR SEQ ID NO:47:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:47:

```
Arg  Ala  Leu  Ala  Glu  Thr  Ser  Tyr  Val  Lys
1                   5                        10
```

( 2 ) INFORMATION FOR SEQ ID NO:48:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:48:

```
Pro  Asp  Ser  Asp  Pro  Ala  Arg  Tyr  Glu  Phe
1                   5                        10
```

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:49:

```
Leu  Glu  Tyr  Val  Ile  Lys  Val  Ser  Ala  Arg
1                   5                        10
```

(2) INFORMATION FOR SEQ ID NO:50:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

```
Arg Gln Val Pro Asp Ser Asp Pro Ala Arg
 1               5                   10
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Phe Phe Pro Ser Leu Arg Glu Ala Ala Leu
 1               5                   10
```

DNA ENCODING MAGE-1 C-TERMINAL CYTOTOXIC T LYMPHOCYTE IMMUNOGENIC PEPTIDES

This is a Division of application Ser. No. 08/103,623 filed Aug. 6, 1993 now abandoned.

BACKGROUND OF THE INVENTION

Tumor cells express certain antigens which are absent from, or present in small amounts on, their normal cellular counterparts. Most of these are differentiation antigens, shared by the tumor and various embryonic cells. Some of the antigens that appear with sufficient selectivity may serve as possible targets for therapeutic agents.

More than 40 different melanoma antigens have been defined with monoclonal antibodies, resulting in several major antigenic families with immunologically and biologically distinct characteristics. Among these families are: (1) the high molecular weight oncofetal proteins; (2) the gangliosides; (3) receptors for growth factors such as EGF, PDGF, TGF-alpha and TGF-beta, and nerve growth factor; (4) cation transport and binding proteins such as p97; (5) HLA class II antigens; (6) pigmentation-associated antigens; and (7) extracellular matrix proteins. Herlyn and Koproski, *Ann. Rev. Immunol.* 6: 283–308 (1988).

While preliminary studies with monoclonal antibody-based therapy and diagnosis directed toward various of these antigens are encouraging, work continues unabated in the hope that better agents and antigenic targets can be identified. Cutaneous malignant melanoma is increasing in prevalence at an alarming rate, particularly in the United States.

More recently a new family of antigens has been described on melanoma tumors. These antigens, now termed the "melanoma antigen," or MAGE family of antigens, were identified in a melanoma cell line which was lysed by a panel of autologous cytotoxic T lymphocytes ("CTLs"). Cells which did not express a MAGE-type antigen were not killed by the CTL, and by selecting these "antigen-loss" variants, six independent antigens were identified. Van den Eynde et al., *Int. J. Cancer*, 44: 634 (1989). A gene encoding one of the antigens, designated MZ2-E ("E") has been cloned and sequenced. Van der Bruggen et al., *Science* 254: 1643 (1991). The sequence was deposited in GenBank (accession #M77481), and comparison of the nucleotide sequence, designated "MAGE-1," failed to reveal any significant homology with any sequence in data banks, including GenBank. Two additional nonidentical cDNAs were also found (MAGE-2 and MAGE-3) which were more closely related to each other than to MAGE-1, but the three were approximately equally expressed.

Smaller regions of the MAGE-1 gene were cloned and transfected into cells. These transfectants expressed antigen which was recognized by the anti-E CTLs. Thus, it appears that the gene does not encode a protein which further activates an antigen-encoding gene. Van der Bruggen, id. The sequence encoding the antigenic peptide was speculated to be within the region of overlap of the segments. See Traversari et al., *J. Exp. Med.* 176: 1453–1457 (1992). The cDNAs of MAGE-2 and MAGE-3 were unable to transfer the expression of antigen E in transfection experiments. The presenting molecule for the E-antigen was thought to be HLA-A1.

The MAGE gene family has been shown by Van der Bruggen et al., id., to be expressed by a variety of different tumors and are not limited to melanomas, but they are not expressed by most normal cells. Thus, the MAGE antigens may have important implications for cancer immunotherapy. The sequence of the MAGE-1 gene was thought to be identical in both normal tissues and in tumors.

What is needed in the art is a more thorough understanding of the immunogenic tumor-rejecting epitopes of the MAGE antigens. Once the immunodominant epitopes are identified, along with their HLA restriction, more effective therapeutic protocols can be devised. The present invention fulfills these and other related needs.

SUMMARY OF THE INVENTION

This invention is based in part on the novel and unexpected observation that the previously reported gene encoding the human MAGE-1 protein encodes an additional fifty-eight amino acids at the C-terminal end. The complete human MAGE-1 protein and peptides thereof can be produced by recombinant or synthetic means and may or may not have the biological activity of the native MAGE-1 antigen, depending on the intended use. Accordingly, isolated and purified polynucleotides are described which code for the complete human MAGE-1 protein. The cDNA which codes for the full length human MAGE-1 protein may be incorporated into a recombinant DNA vector; which in turn may be used to transform a suitable host; the host cell transformed with the vector including the cDNA can express full length human MAGE-1 protein, and the full length human MAGE-1 protein can be recovered.

This invention further concerns MAGE-1 immunogenic peptides from the C-terminus of the MAGE-1 protein which induce CTL activity. The immunogenic peptides of this invention may be identified using motifs as described in copending U.S. patent applications Ser. No. 07/926,666 (now abandoned) and Ser. No. 08/027,146 (now abandoned) for the various MHC class I alleles. Thus, small synthetic or recombinant peptides can be prepared which immunologically mimic MAGE-1 CTL inducing antigenic determinants. The CTL-inducing MAGE-1 peptides of the invention can be used therapeutically, for example, to induce, in the context of an appropriate MHC presenting molecule, an immunological response to tumors which express the corresponding MAGE determinants. In this manner the tumor cells can be killed or inhibited. The induction of CTLs can be accomplished in vivo or ex vivo. Thus, the MAGE-1 peptides described herein also can be formulated and administered as pharmaceutical compositions, especially when used to induce immunological responses in individuals predisposed to developing or already afflicted by a tumor which expresses MAGE-1 determinants.

In yet other embodiments the invention relates to methods for diagnosis, where the peptides of the invention are used to determine the presence in an individual of lymphocytes which are capable of a cytotoxic T cell response to MAGE-1 antigen. Typically the lymphocytes are peripheral blood lymphocytes and the individual of interest is suffering from a tumor associated with MAGE antigen. The diagnostic methods and compositions can be used in conjunction with therapeutic approaches to MAGE related diseases, and particularly the treatment of malignant melanoma.

BRIEF DESCRIPTION OF THE DRAWINGS

FIGS. 1A–F is the nucleotide and amino acid sequence of full length human MAGE-1 protein (see Seq. ID Nos. 23 and 24).

FIG. 2 is the nucleotide and amino acid sequence of the newly discovered C terminal portion of the full length human MAGE-1 protein (included within Seq. ID Nos. 23 and 24).

FIGS. 3A–C illustrate CTL responses specific for certain newly identified peptides from the C-terminus portion of the human MAGE-1 protein (FIG. 3A: Seq. ID No. 28; FIG. 3B: Seq. ID No. 32; FIG. 3C: Seq. ID No. 47).

DESCRIPTION OF THE SPECIFIC EMBODIMENTS

Figure 3A:
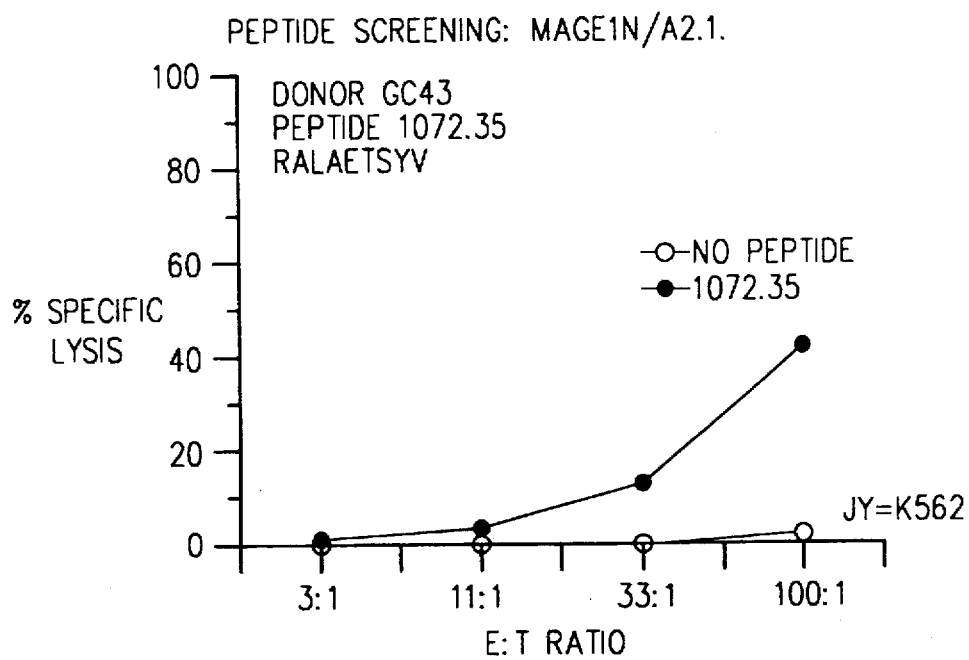

The melanoma antigen termed "MAGE" was identified in the context of a CTL-inducing antigen. The MAGE antigen has since been discovered to be a family of related antigens expressed by a variety of tumor cells. The present invention provides the complete nucleotide sequence encoding human MAGE-1 antigen and the complete amino acid sequence thereof, thereby providing for the ultimate expression of the complete human MAGE-1 protein and new MAGE-1 peptides which have immunological activity. Recombinant DNA expression systems and chemical synthetic methods provide convenient means for obtaining large quantities of recombinant human MAGE-1 and the peptide fragments thereof in relatively pure form.

In preferred embodiments the peptides of the invention are derived from the region of the MAGE-1 antigen of the C-terminal 58 amino acids, as set forth in Seq. ID No. 1:

Seq. ID No. 1

Arg-Gln-Val-Pro-Asp-Ser-Asp-Pro-Ala-Arg-Tyr-Glu-Phe-Leu-Trp-Gly-Pro-Arg-Ala-Leu-Ala-Glu-Thr-Ser-Tyr-Val-Lys-Val-Leu-Glu-Tyr-Val-Ile-Lys-Val-Ser-Ala-Arg-Val-Arg-Phe-Phe-Phe-Pro-Ser-Leu-Arg-Glu-Ala-Ala-Leu-Arg-Glu-Glu-Glu-Glu-Gly-Val

The peptide which is selected from the region of Seq. ID No. 1 induces MHC HLA class I-restricted CTL responses to MAGE expressing cells. The stimulated CTL, which secrete lymphokines (e.g., gamma interferon) and liberate products (e.g., proteolytic enzymes such as serine esterases) that inhibit viral replication in infected autologous cells or transfected cells, with or without cell killing, are able to interrupt or substantially prevent the growth of MAGE expressing tumor cells. In many instances the combination of an effective cytotoxic T cell response and a protective antibody response to selected tumor antigens will be preferred for treating a MAGE-associated tumor.

In more preferred embodiments described herein an immunity-inducing peptide derived from the region of Seq. ID No. 1 has at least seven amino acids wherein a majority of amino acids of the peptide will be identical or substantially homologous, when compared to the amino acids comprising the corresponding portion of the naturally occurring MAGE-1 sequence. Representative peptides of this region are set forth in Table 1 below with MHC restriction indicated.

The peptide can be optionally flanked and/or modified at one or both of the N- and C-termini, as desired, by amino acids from MAGE sequences, particularly MAGE-1, amino acids added to facilitate linking, other N- and C-terminal modifications, linked to carriers, etc., as further described herein. The peptide induces a CTL response which is mediated by at least the MHC class I molecule as indicated above.

The term "peptide" is used interchangeably with "oligopeptide" in the present specification to designate a series of residues, typically L-amino acids, connected one to the other typically by peptide bonds between the alpha-amino and carbonyl groups of adjacent amino acids. The oligopeptides of the invention are less than about 15 residues in length and usually consist of between about 8 and about 11 residues, preferably 9 or 10 residues.

By "immunogenic peptide" of the present invention is meant a peptide which comprises an allele-specific motif such that the peptide will bind the MHC allele and be capable of inducing a CTL response. The immunogenic peptides of this invention are derived from selected epitopic regions of the C-terminal 58 amino acid residues of the MAGE-1 antigen. The immunogenic peptides are capable of binding to an appropriate class I MHC molecule and inducing a cytotoxic T cell response against the MAGE antigen from which the immunogenic peptide is derived.

A "conserved residue" is an amino acid which occurs in a significantly higher frequency than would be expected by random distribution at a particular position in a peptide motif. Typically a conserved residue is one at which the immunogenic peptide may provide a contact point with the MHC molecule. One to three, preferably two, conserved residues within a peptide of defined length defines a motif for an immunogenic peptide. These residues are typically in close contact with the peptide binding groove, with their side chains buried in specific pockets of the groove itself. Typically, an immunogenic peptide will comprise up to three conserved residues, more usually two conserved residues.

As used herein, "negative binding residues" are amino acids which if present at certain positions will result in a peptide being a nonbinder or poor binder and in turn fail to induce a CTL response despite the presence of the appropriate conserved residues within the peptide.

The term "motif" refers to the pattern of residues in a peptide of defined length, usually about 8 to about 11 amino acids, which is recognized by a particular MHC allele. The peptide motifs are typically different for each human MHC allele and differ in the pattern of the highly conserved residues.

The binding motif for an allele can be defined with increasing degrees of precision. In one case, all of the conserved residues are present in the correct positions in a peptide and there are no negative binding residues present.

The phrases "isolated" or "biologically pure" refer to material which is substantially or essentially free from components which normally accompany it as found in its native state. Thus, the peptides of this invention do not contain materials normally associated with their in situ environment, e.g., MHC I molecules on antigen presenting cells. Even where a protein has been isolated to a homogenous or dominant band, there are trace contaminants in the range of 5–10% of native protein which co-purify with the desired protein. Isolated peptides of this invention do not contain such endogenous co-purified protein.

The term "residue" refers to an amino acid or amino acid mimetic incorporated in a oligopeptide by an amide bond or amide bond mimetic.

Peptides comprising the CTL epitopes are synthesized and the ability to bind appropriate MHC molecules is determined in assays using, for example, purified class I molecules and radioiodinated peptides and/or cells expressing empty class I molecules by, for instance, immunofluorescent staining and flow microfluorimetry, peptide-dependent class I assembly assays, and inhibition of CTL recognition by peptide competition. Those peptides that bind to the class I molecule are further chosen for their ability to serve as targets for CTLs derived from afflicted individuals, as well as for their capacity to induce primary in vitro or in vivo CTL responses that can give rise to CTL populations capable of reacting with tumor cells as therapeutic agents. Methods for determining allele-specific peptides and peptide motifs are described in co-pending commonly owned applications U.S. Ser. No. 027,146 (now abandoned) and U.S. Ser. No. 027,746 (now abandoned), which are incorporated herein by reference.

The peptides or oligopeptides can be prepared "synthetically," as described herein below, or by recombinant DNA technology. Although the peptide will preferably be substantially free of other naturally occurring human proteins and fragments thereof, in some embodiments the peptides can be conjugated to other MAGE fragments or other proteins or peptides which contribute directly or indirectly to an anti-tumor immunological response. The term peptide or oligopeptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. When possible, it may be desirable to optimize peptides of the invention to a length of nine or ten amino acid residues, commensurate in size with processed peptides that are bound to MHC class I molecules on the cell surface. See generally, Schumacher et al., *Nature* 350:703–706 (1991); Van Bleek et al., *Nature* 348:213–216 (1990); Rotzschke et al., *Nature* 348:252–254 (1990); and Falk et al., *Nature* 351:290–296 (1991), which are incorporated herein by reference. By biological activity is meant the ability to bind an appropriate MHC molecule and, in the case of peptides useful for stimulating CTL responses, induce a CTL response against MAGE antigen or antigen mimetic. In the case of a peptide analog antagonist, the analog will have biological activity if it competes with the peptide for binding to the MHC molecule and has a substantially reduced ability to stimulate a CTL response when compared to the native peptide. By a CTL response is meant a $CD8^+$ T lymphocyte response specific for the MAGE antigen of interest, e.g., members of the MAGE antigen family, wherein $CD8^+$, MHC class I-restricted T lymphocytes are activated. As noted above, the activated T lymphocytes will secrete a variety of products which inhibit tumor cell replication and may or may not directly kill the tumor cell or other transfected cell which expresses the appropriate MAGE antigenic determinant(s).

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

The peptides of the present invention or analogs thereof which have CTL stimulating activity may be modified to provide desired attributes other than improved serum half life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated.

In some embodiments it may be desirable to include in the pharmaceutical compositions of the invention at least one component which assists in priming CTL. Lipids have been identified as agents capable of assisting the priming CTL in vivo against certain antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime specific CTL when covalently attached to an appropriate peptide. See, e.g., Deres et al., *Nature* 342:561–564 (1989), incorporated herein by reference. Peptides of the invention can be coupled to $P_3CSS$, for example, and the lipopeptide administered to an individual to specifically prime a CTL response to the target antigen. Further, as the induction of neutralizing antibodies can also be primed with $P_3CSS$ conjugated to a peptide which displays an appropriate epitope, the two compositions can be combined to more effectively elicit both humoral and cell-mediated responses to MAGE antigen.

As mentioned above, additional amino acids can be added to the termini of an oligopeptide or peptide to provide for ease of linking peptides one to another, for coupling to a carrier, support or larger peptide, for reasons discussed herein, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. In addition, the peptide or oligopeptide sequences can differ from the natural sequence by being modified by terminal-$NH_2$ acylation, e.g., by alkanoyl ($C_1$–$C_{20}$) or thioglycolyl acetylation, terminal-carboxy amidation, e.g., ammonia, methylamine, etc. In some instances these modifications may provide sites for linking to a support or other molecule.

It will be understood that the peptides of the present invention or analogs thereof which have CTL and/or T helper stimulating activity may be modified to provide other desired attributes, e.g., improved pharmacological characteristics, while increasing or at least retaining substantially all of the biological activity of the unmodified peptide. For instance, the peptides can be modified by extending, decreasing or substituting in the peptides amino acid sequences by, e.g., the addition or deletion of amino acids on either the amino terminal or carboxy terminal end, or both, of peptides derived from the sequences disclosed herein. The CTL activity of the subject peptides can be enhanced by linkage to a sequence which contains at least one epitope that is capable of inducing a T helper cell response, as explained above.

The peptides employed in the subject invention need not be identical to those exemplary peptides identified above or to a particular MAGE or MAGE-1 protein sequence, so long as the subject compounds are able to bind to the appropriate MHC molecule and provide for cytotoxic T lymphocytic or T helper activity against cells which express a MAGE antigen. Therefore, the peptides may be subject to various changes, such as insertions, deletions, and substitutions, either conservative or non-conservative, where such changes might provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic a MAGE CTL or T helper stimulating epitope will not differ by more than about 20% from the sequence of at least one member of the MAGE family, except where additional amino acids may be added at either terminus for the purpose of modifying the physical or chemical properties of the peptide for, e.g., ease of linking or coupling, and the like. In those situations where regions of the peptide sequences are found to be polymorphic among MAGE antigens, it may be desirable to vary one or more particular amino acids to more effectively mimic differing cytotoxic T-lymphocyte or T helper epitopes of different MAGE antigens.

Using the methods described herein, two or more peptides may be identified which define different or overlapping CTL or T helper epitopes from a particular region. For example, using the methods described herein, two or more peptides may define different or overlapping CTL or T helper epitopes from a particular region, e.g., the peptide region of the C-terminus of MAGE-1, or of a different region, which peptides can be combined in a "cocktail" to provide enhanced immunogenicity for CTL or T helper-mediated responses. Peptides of one region can also be combined with peptides having different MHC restriction elements. This composition can be used to effectively broaden the immunological coverage provided by therapeutic, vaccine or diagnostic methods and compositions of the invention among a diverse population. When the peptides are linked, by covalent or non-covalent means, it will be understood that linkage should not substantially interfere with either of the linked groups to function as described, e.g., to function as a MAGE cytotoxic T cell determinant or MAGE T helper determinant.

In another aspect the peptides of the invention can be combined or coupled with other peptides which present MAGE T helper cell epitopes, i.e., T helper peptides comprising six to thirty amino acids containing a T helper epitope from a MAGE protein or other immunogenic protein or derivative thereof to stimulate T cells that cooperate in the induction of immune response against the MAGE antigen, e.g., in the CTL response to MAGE determinants. The T-helper cells can be either the T-helper 1 or T-helper 2 phenotype, for example. Compositions of T-helper peptides and CTL peptides thereby enhance an individual's immunity by providing cell-mediated immunity and protective antibodies to MAGE antigen. T helper epitopes can be provided by peptides from, for example, tetanus toxoid $_{830-843}$ having the sequence Gln-Tyr-Ile-Lys-Ala-Asn-Ser-Lys-Phe-Ile-Gly-Ile-Thr-Glu (QYIKANSKFIGITE) [Seq. ID No. 18]; malaria circumsporozoite $_{382-398}$ Lys-Ile-Ala-Lys-Met-Lys-Ala-Ser-Ser-Val-Phe-Asn-Val-Val-Asn-Ser (KIAKMEKASSVFNVVNS) [Seq. ID No. 19]; malaria circumsporozoite $_{378-398}$ Asp-Ile-Glu-Lys-Lys-Ile-Ala-Lys-Met-Lys-Ala-Ser-Ser-Val-Phe-Asn-Val-Val-Asn-Ser (DIEKKIAKMEKASSVFNVVNS) [Seq. ID No. 20]; ovalbumin $_{323-336}$ Ile-Ser-Gln-Ala-Val-His-Ala-Ala-His-Ala-Glu-Ile-Asn-Glu [Seq. ID No. 21], the influenza epitope $_{307-319}$ Pro-Lys-Tyr-Val-Lys-Gln-Asn-Thr-Leu-Lys-Leu-Ala-Thr [Seq. ID No. 22], and others.

In preferred embodiments the CTL inducing peptides of the invention are covalently linked to the T helper peptides. Particularly preferred CTL inducing peptides/T helper conjugates are linked by a spacer molecule. Alternatively, the CTL peptide may be linked to the T helper peptide without a spacer. The T helper peptide is conjugated to the CTL peptide, preferably with the T helper peptide positioned at the amino terminus. The peptides may be joined by a neutral linker, such as Ala-Ala-Ala or the like, and preferably further contains a lipid residue such as palmitic acid or the like which is attached to alpha and epsilon amino groups of a Lys residue ((PAM)$_2$Lys), which is attached to the amino terminus of the peptide conjugate, typically via Ser-Ser linkage or the like.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference.

Alternatively, recombinant DNA technology may be employed wherein a nucleotide sequence which encodes a CTL peptide and/or T helper peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, which disclosures are incorporated herein by reference. Thus, fusion proteins which comprise one or more peptide sequences of the invention can be used to present the MAGE-1 CTL determinants. For example, a recombinant MAGE antigen polypeptide is prepared in which the amino acid sequence is altered so as to more effectively present epitopes of peptide regions described herein to stimulate a CTL response.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression, the coding sequence will be provided with operably linked start and stop codons, promoter and terminator regions and usually a replication system to provide an expression vector for expression in the desired cellular host. Of course, bacterial, yeast or mammalian cell hosts may be used, employing suitable vectors and control sequences.

The complete MAGE-1 DNA sequence or fragments encoding the C-terminal 58 amino acids of the MAGE-1 protein as described herein may be introduced into cultured mammalian cells by a variety of means, as will be recognized by those skilled in the art. For example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973), electroporation (Neumann et al., EMBO J. 1: 841–845, 1982), or DEAE-dextran mediated transfection (Ausubel et al., (ed.) Current Protocols in Molecular Biology, John Wiley and Sons, Inc., NY (1987), incorporated herein by reference) may find convenient use. To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. Further, the selectable marker may be an amplifiable selectable marker, and preferred amplifiable selectable markers include the DHFR gene and the neomycin resistance gene. Selectable markers are reviewed by Thilly (Mammalian Cell Technology, Butterworth Publishers, Stoneham, Mass., which is incorporated herein by reference).

Transfected mammalian cells are allowed to grow for a period of time, typically 1–2 days, to begin expressing the MAGE-1 DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods for introducing expression vectors encoding foreign proteins such as human MAGE-1 into plant, avian and insect cells are also well known in the art. Techniques for transforming fungi are well known in the literature, and have been described, for instance, by Beggs (Nature 275:104–108 (1978)), Hinnen et al. (Proc. Natl. Acad. Sci. USA 75: 1929–1933, 1978), Yelton et al. (Proc. Natl. Acad. Sci. USA 81: 1740–1747, 1984), Russell (Nature 301: 167–169, 1983) and U.S. Pat. No. 4,935,349, incorporated herein by reference. Suitable yeast vectors for use in the present invention will generally include a selectable marker, which may be one of any number of genes that exhibit a dominant phenotype for which a phenotypic assay exists to enable transformants to be selected.

Host cells containing DNA constructs which encode the complete MAGE-1 protein of the present invention or C-terminal fragments thereof are then cultured to produce the protein or peptides. The cells are cultured according to standard methods in a culture medium containing nutrients required for growth of the chosen host cells. A variety of suitable media are known in the art. The growth medium will generally select for cells containing the DNA construct by, for example, drug selection or deficiency in an essential nutrient which is complemented by the selectable marker on the DNA construct or co-transfected with the DNA construct. Selection of a medium appropriate for the particular cell line used is within the level of ordinary skill in the art. Cultured mammalian cells are generally cultured in commercially available serum-containing or serum-free media.

The complete MAGE-1 protein and C-terminal fragments thereof produced according to the present invention may be purified by, e.g., affinity chromatography on an antibody column using antibodies, preferably monoclonal antibodies, directed against corresponding MAGE epitopes. Additional purification may be achieved by conventional chemical purification means, such as liquid chromatography, gradient centrifugation, and gel electrophoresis, among others. Methods of protein purification are known in the art (see generally, Scopes, R., Protein Purification, Springer-Verlag, NY (1982), which is incorporated herein by reference) and may be applied to the purification of the recombinant human MAGE-1 described herein. Substantially pure recombinant human MAGE-1 of at least about 50% is preferred, at least about 70–80% more preferred, and 95–99% or more homogeneity most preferred, particularly for pharmaceutical uses. Once purified, partially or to homogeneity, as desired, the recombinant human MAGE may then be used diagnostically, therapeutically, etc. as described herein.

The peptides of the present invention and pharmaceutical and vaccine compositions thereof are useful for administration to mammals, including humans, to treat and/or prevent tumors associated with expression of MAGE antigen.

For pharmaceutical compositions, the peptides, i.e., the CTL or T helper peptides or CTL/T helper peptide conjugates, as described above will be administered to an individual already suffering from a MAGE-associated tumor.

Those in the early stages of tumor development can be treated with the immunogenic peptides separately or in conjunction with other treatments, as appropriate. In therapeutic applications, compositions are administered to a patient in an amount sufficient to elicit an effective CTL response to a MAGE-bearing tumor and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 500 µg of peptide for a 70 kg patient, followed by boosting dosages of from about 1.0 µg to about 100 µg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of CTL or T helper stimulatory peptides of the invention sufficient to effectively treat the patient.

As individuals may develop MAGE-associated tumors because of an inadequate (or absent) CTL or T helper response during the earliest stages of tumor development, it is important to provide an amount of immuno-potentiating peptide in a formulation and mode of administration sufficient to effectively stimulate a CTL or T helper cell response. Administration should continue until at least clinical symptoms or laboratory indicators indicate that the tumor has been eliminated or its progression has substantially abated and for a period thereafter. Immunizing doses followed by boosting doses at established intervals, e.g., from one to four weeks, may be required, possibly for a prolonged period of time, as necessary to resolve the tumor.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the CTL or T helper stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Certain lipids are capable of priming CTL responses in vivo, e.g., palmitic acid residues can be attached to the alpha and epsilon amino groups of a Lys residue and then linked to a synthetic peptide which comprises a class I-restricted CTL epitope. As further described herein, the lipidated peptide can then be incorporated into a liposome emulsified in an adjuvant, e.g., incomplete Freund's adjuvant. The arrangement of the components of the conjugate comprising the CTL inducing peptide/T helper peptide/lipid can be varied. In one case, the lipid moiety can be linked to the amino terminal end of the CTL inducing peptide, which in turn is linked at its carboxy terminal to the T helper peptide. In another case, the lipid is linked at the amino terminal end of the T helper peptide, which is linked at its carboxy terminal to the CTL inducing peptide. In each case, a spacer molecule, e.g., Lys-Ser-Ser, can be selectively inserted between the lipid moiety and the CTL or T helper peptide, as well as between the T helper and the CTL inducing peptides.

The concentration of CTL stimulatory peptides of the invention in the pharmaceutical formulations can vary widely, i.e., from less than about 1%, usually at or up to at least about 10%, to as much as 20 to 50% or more by weight, and will be selected primarily by fluid volumes, viscosities, etc., in accordance with the particular mode of administration selected. Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Sciences*, 17th ed., Mack Publishing Company, Easton, Pa. (1985), which is incorporated herein by reference.

The peptides of the invention may also be administered via liposomes. Liposomes, which include emulsions, foams, micelles, insoluble monolayers, phospholipid dispersions, lamellar layers and the like, can serve as a vehicle to target the peptides to a particular tissue, such as lymphoid tissue, or to tumor cells, as well as to increase the half-life of the peptide composition. In these preparations the peptide to be delivered is incorporated as part of a liposome, alone or in conjunction with a molecule which binds to, e.g., a receptor prevalent among lymphoid cells or tumor cells, such as monoclonal antibodies, or with other therapeutic or immunogenic compositions. A variety of methods are available for preparing liposomes, as described in, e.g., U.S. Pat. Nos. 4,837,028 and 5,019,369, incorporated herein by reference.

In another aspect the present invention is directed to vaccines which contain as an active ingredient an immunogenically effective amount of a CTL stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of MAGE proteins. Useful carriers are well known in the art, and include, e.g., thyroglobulin, albumins such as human serum albumin, tetanus toxoid, polyamino acids such as poly(D-lysine:D-glutamic acid), influenza, hepatitis B virus core protein, and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. Upon immunization with a peptide composition as described herein, via injection, aerosol, oral, transdermal or other route, the immune system of the host responds to the vaccine by producing large amounts of CTLs specific for MAGE antigen, and the host becomes at least partially immune to MAGE-bearing tumors or resistant to such tumors.

Vaccine compositions containing the peptides of the invention are administered to a patient susceptible to or otherwise at risk of developing MAGE-associated tumors, such as melanomas, to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 µg to about 500 µg per 70 kilogram patient, more commonly from about 50 µg to about 100 µg mg per 70 kg of body weight. CTL-inducing peptides are administered to individuals of an appropriate HLA type. In some instances it may be desirable to combine the peptide vaccines of the invention with vaccines which induce neutralizing cellular or antibody responses to tumor antigens, such as the p97 tumor antigen, for example.

For therapeutic or immunization purposes, the peptides of the invention can also be expressed by attenuated viral hosts, e.g., vaccinia or fowlpox. This approach involves the use of vaccinia virus as a vector to express nucleotide sequences that encode the peptides or conjugates of the invention. Upon introduction into a host, the recombinant vaccinia virus expresses the MAGE peptide, and thereby elicits a host CTL or T helper response to MAGE antigen on the tumor cells. Vaccinia vectors and methods useful in immunization protocols are described in, e.g., U.S. Pat. No. 4,722,848, incorporated herein by reference. A wide variety of other vectors useful for therapeutic administration or immunization of the peptides of the invention will be apparent to those skilled in the art from the description herein.

The immunogenic peptides of the invention may be used to elicit CTL ex vivo. The resulting CTL can be used to treat tumors in patients that do not respond to other conventional forms of therapy, or will not respond to a peptide vaccine approach of therapy. Ex vivo CTL responses to a MAGE expressing tumor are induced by incubating in tissue culture a patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will inhibit or kill targeted tumor cells.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing MAGE-associated tumors.

The following examples are offered by way of illustration, not by way of limitation.

EXAMPLE 1

Cloning of Full Length MAGE DNA

The predicted coding region of MAGE-1 was cloned from first strand cDNA synthesized from the MAGE-1 positive cell line 938 by PCR amplification using primers located at bp605–622 and bp1459–1476. The amplification was carried out using a high fidelity thermostable polymerase, Pfu, by cycling 30 times, 2 minutes at 95° C., 2 minutes at 50° C., and 2 minutes at 73° C. These conditions resulted in the amplification of a 870 bp fragment consistent with the predicted size for MAGE-1. The amplified fragment was subcloned in the vector pRc/RSV (Invitrogen) for further characterization.

The cloned fragment was sequenced using sequenase (v 2.0, USB) and MAGE-1 specific primers. Sequence characterization of the cloned fragment found a cytidine inserted at nucleotide 1377. This insertion falls immediately 3' of the sequence.

To determine if the insertion had been introduced during PCR amplification the genomic sequence of MAGE-1 from the original cell line as well as from four independent normal individuals was determined. Genomic DNA was isolated and the MAGE-1 gene was amplified using the same conditions used in the original cloning. The amplified fragment was cycle sequenced using an antisense primer corresponding to nucleotides 1427–1448. The procedures were as follows.

Genomic DNA Isolation: Cells from the MAGE-1 expressing cell line were taken directly from tissue culture stocks. The procedure for genomic DNA isolation from individuals was as follows: 15 mls of heparinized whole blood was mixed with 15 mls of RPMI 1640 media and layered over 20 mls of lymphocyte separation media and centrifuged for 15 minutes at 400×g following the manufacturers protocol (FICOLL-PAQUE, Pharmacia). The cell layer was collected and washed twice in RPMI 1640 media. The lymphocytes were counted, resuspended at $4 \times 10^6$ cells/ml in 90% fetal bovine serum, 10% dimethyl sulfoxide and stored under liquid nitrogen until further processing.

The thawed cell pellet was lysed in 400 µl of lysis buffer (4.2M guanidine thiocyanate, 25.5 mM sodium acetate, 122 mM β-mercaptoethanol). The lysate was extracted once with an equal volume of phenol/chloroform and then an equal volume of chloroform. Sodium acetate was added to a final concentration of 0.3M and the DNA was precipitated with two volumes of ethanol. The purified genomic DNA was resuspended in 200 µl of $H_2O$. The DNA concentration was determined by fluorometry following the directions provided by the manufacturer (TKO 0100 Fluorometer, Hoeffer).

DNA Amplification

A 100 µl reaction mix was prepared containing 0.5 µg of genomic DNA, 0.5 µM of each amplification primer (primers indicated above), 10 mM Tris-HCl (pH 8.8), 50 mM KCl, 1.5 mM $MgCl_2$, 0.001% (w/v) gelatin, all four deoxyribonucleotide triphosphates (dNTPs) each at 500 µM, add 1.25 units of Taq DNA polymerase (Stratagene). The incubation conditions used were: 30 cycles of 95° C., 2 minutes, 50° C., 2 minutes, 72° C., 2 minutes.

PCR DNA Fragment Purification

The 100 µl reaction mix was fractionated by electrophoresis through a 1% agarose (SeaKem Agarose, FMC Inc.) gel, containing 10 µg/ml ethidium bromide, 40 mM Tris-acetate, 1 mM EDTA. A gel slice containing the desired DNA fragment (870 bp for the MAGE-1 amplified fragment) was excised during UV illumination. The DNA was purified using a glass bead purification kit (Qiaex, Qiagen) and was eluted in 20 µl of $H_2O$.

DNA Sequencing

All of the eluted DNA was sequenced with the appropriate primer (49 nucleotides downstream of the MAGE-1 amplified fragment) following the [$^{35}S$]dCTP incorporation protocol recommended by the manufacturers of the commercial cycle-sequencing kit (ΔTaq Cycle-Sequencing Kit, Untied States Biochemical). The sequencing reactions were fractionated by electrophoresis through a 8% polyacrylamide gel (0.4 mm thick). The polyacrylamide gel was dried and exposed to X-ray film (XAR-5, Kodak) for 16 to 48 hours.

Each of the five MAGE 1 genes sequences contained the cytidine insertion at nucleotide 1377 when compared to the sequence in the GenBank entry. The insertion is significant because it shifts the reading frame of the gene, which changes 25 C-terminal amino acids and also extends the protein for an additional 33 amino acids. The full length DNA and amino acid sequence of human MAGE-1 protein is shown in FIG. 1. FIG. 2 shows the nucleotide and amino acid sequence of the newly discovered C terminal portion to the human MAGE-1 protein.

EXAMPLE 2

Identification of MAGE Immunogenic Peptides from the C-Terminus

Using motifs for the various MHC class I alleles the C-terminus of the MAGE protein was analyzed for the presence of the motifs.

The motif for HLA-A3.2 comprises from the N-terminus to C-terminus a first conserved residue of L, M, I, V, S, A, T and F at position 2 and a second conserved residue of K, R or Y at the C-terminal end. Other first conserved residues are C, G or D and alternatively E. Other second conserved residues are H or F. The first and second conserved residues are preferably separated by 6 to 7 residues.

The motif for HLA-A1 comprises from the N-terminus to the C-terminus a first conserved residue of T, S or M, a second conserved residue of D or E, and a third conserved residue of Y. Other second conserved residues are A, S or T. The first and second conserved residues are adjacent and are preferably separated from the third conserved residue by 6 to 7 residues. A second motif consists of a first conserved residue of E or D and a second conserved residue of Y where the first and second conserved residues are separated by 5 to 6 residues.

The motif for HLA-A11 comprises from the N-terminus to the C-terminus a first conserved residue of T or V at position 2 and a C-terminal conserved residue of K. The first and second conserved residues are preferably separated by 6 or 7 residues.

The motif for HLA-A24.1 comprises from the N-terminus to the C-terminus a first conserved residue of Y, F or W at position 2 and a C terminal conserved residue of F, I, W, M or L. The first and second conserved residues are preferably separated by 6 to 7 residues.

The motif for HLA-A2.1 for 9 mer peptides includes one of the amino acids I, V, A and T at position L and V, L, I, A and M at position 9. Neither acidic amino acids nor P were found in position 1. only one acidic amino acid and no basic amino acids were found in position 3. Positions 6 and 7 showed no charged residues. Acidic amino acids, however, were frequently found in position 8, where they are tolerated, according to our definition of the A2.1 motif. The analysis of the sequences of naturally processed peptides therefore reveals that >90% of the peptides followed the defined rules for a complete motif.

The motif for HLA-A2.1 for 10 mer peptides includes one of the amino acids L, M, I, V, A and T at position 2 and V; I, L, A and M at position 10. In position 1 for example, in 10-mers again the P residue and acidic amino acids were not tolerated. In addition at position 1 in 10-mers aromatic residues were frequently observed in A2.1 binders. In position 3, acidic amino acids were frequently associated with poor binding capacity in both 9-mers and 10-mers. Interestingly, however, while in position 3 aromatic residues were preferred in 9-mers, aliphatic residues (L, V, I, M) were preferred in 10-mers.

The immunogenic peptides of about 9 and 10 amino acids in length identified using the motifs are set forth in Table 1.

TABLE 1

| Antigen | Position | Sequence | Size | Seq ID # | Allele |
| --- | --- | --- | --- | --- | --- |
| MAGE1N | 274 | TSYVKVLEY | 9 | 3 | A01 |
| MAGE1N | 254 | VPDSDPARY | 9 | 10 | A01 |
| MAGE1N | 268 | PRALAETSY | 9 | 25 | A01 |
| MAGE1N | 301 | ALREEEEGV | 9 | 6 | A02 |
| MAGE1N | 264 | FLWGPRALA | 9 | 5 | A02 |
| MAGE1N | 276 | YVKVLEYVI | 9 | 26 | A02 |
| MAGE1N | 289 | RVRFFFPSL | 9 | 11 | A02 |
| MAGE1N | 278 | KVLEYVIKV | 9 | 4 | A02 |
| MAGE1N | 282 | YVIKVSARV | 9 | 27 | A02 |
| MAGE1N | 269 | RALAETSYV | 9 | 28 | A02 |
| MAGE1N | 271 | LAETSYVKV | 9 | 29 | A02 |

TABLE 1-continued

| Antigen | Position | Sequence | Size | Seq ID # | Allele |
| --- | --- | --- | --- | --- | --- |
| MAGE1N | 253 | QVPDSDPAR | 9 | 30 | A03 |
| MAGE1N | 285 | KVSARVRFF | 9 | 31 | A03 |
| MAGE1N | 270 | ALAETSYVK | 9 | 32 | A03 |
| MAGE1N | 283 | VIKVSARVR | 9 | 33 | A03 |
| MAGE1N | 295 | PSLREAALR | 9 | 34 | A03 |
| MAGE1N | 274 | TSYVKVLEY | 9 | 3 | A03 |
| MAGE1N | 256 | DSDPARYEF | 9 | 35 | A03 |
| MAGE1N | 286 | VSARVRFFF | 9 | 36 | A03 |
| MAGE1N | 253 | QVPDSDPAR | 9 | 30 | A11 |
| MAGE1N | 283 | VIKVSARVR | 9 | 33 | A11 |
| MAGE1N | 295 | PSLREAALR | 9 | 34 | A11 |
| MAGE1N | 274 | TSYVKVLEY | 9 | 3 | A11 |
| MAGE1N | 270 | ALAETSYVK | 9 | 32 | A11 |
| MAGE1N | 244 | VQEKYLEYR | 9 | 37 | A11 |
| MAGE1N | 263 | EFLWGPRAL | 9 | 38 | A24 |
| MAGE1N | 273 | ETSYVKVLEY | 10 | 2 | A01 |
| MAGE1N | 270 | ALAETSYVKV | 10 | 7 | A02 |
| MAGE1N | 279 | VLEYVIKVSA | 10 | 39 | A02 |
| MAGE1N | 271 | LAETSYVKVL | 10 | 40 | A02 |
| MAGE1N | 300 | AALREEEEGV | 10 | 41 | A02 |
| MAGE1N | 276 | YVKVLEYVIK | 10 | 42 | A03 |
| MAGE1N | 243 | LVQEKYLEYR | 10 | 43 | A03 |
| MAGE1N | 282 | YVIKVSARVR | 10 | 15 | A03 |
| MAGE1N | 289 | RVRFFFPSLR | 10 | 44 | A03 |
| MAGE1N | 253 | QVPDSDPARY | 10 | 45 | A03 |
| MAGE1N | 285 | KVSARVRFFF | 10 | 46 | A03 |
| MAGE1N | 242 | DLVQEKYLEY | 10 | 14 | A03 |
| MAGE1N | 283 | VIKVSARVFR | 10 | 33 | A03 |
| MAGE1N | 269 | RALAETSYVK | 10 | 47 | A03 |
| MAGE1N | 273 | ETSYVKVLEY | 10 | 2 | A03 |
| MAGE1N | 255 | PDSDPARYEF | 10 | 48 | A03 |
| MAGE1N | 280 | LEYVIKVSAR | 10 | 49 | A03 |
| MAGE1N | 276 | YVKVLEYVIK | 10 | 42 | A11 |
| MAGE1N | 243 | LVQEKYLEYR | 10 | 43 | A11 |
| MAGE1N | 282 | YVIKVSARVR | 10 | 15 | A11 |
| MAGE1N | 289 | RVRFFFPSLR | 10 | 44 | A11 |
| MAGE1N | 253 | QVPDSDPARY | 10 | 45 | A11 |
| MAGE1N | 269 | RALAETSYVK | 10 | 47 | A11 |
| MAGE1N | 273 | ETSYVKVLEY | 10 | 2 | A11 |
| MAGE1N | 252 | RQVPDSDPAR | 10 | 50 | A11 |
| MAGE1N | 280 | LEYVIKVSAR | 10 | 49 | A11 |
| MAGE1N | 275 | SYVKVLEYVI | 10 | 17 | A24 |
| MAGE1N | 293 | FFPSLREAAL | 10 | 51 | A24 |
| MAGE1N | 271 | LAETSYVKVL | 10 | 40 | A24 |

These peptides were then evaluated as to their capacity to bind to the appropriate class I molecules using specific binding assays as described in copending and commonly owned application U.S. Ser. No. 08/027,746 (now abandoned), incorporated herein by reference. Results of the binding assays are set forth in table 2.

TABLE 2

| | | | | MAGE CTL TARGETS | | | | | |
|---|---|---|---|---|---|---|---|---|---|
| Sequence | Seq ID # | Posit. | Motif | Size | A1 | A2 | A3 | A11 | A24 | Id |
| ETSYVKVLEY | 2 | 274 | A01/11 | 10 | 0.5600 | | | | | 1072.28 |
| TSYVKVLEY | 3 | 275 | A01/11 | 9 | 0.0990 | | | | | 1072.29 |
| KVLEYVIKV | 4 | 279 | A02 | 9 | | 0.0900 | | | | 1072.30 |
| FLWGPRALA | 5 | 265 | A02 | 9 | | 0.0420 | | | | 1072 31 |
| ALREEEEGV | 6 | 302 | A02 | 9 | | 0.0210 | | | | 1072.32 |
| ALAETSYVKV | 7 | 271 | A02 | 10 | | 0.0150 | | | | 1072.33 |
| YVIKVSARV | 27 | 283 | A02 | 9 | | 0.0140 | | | | 1072.34 |
| RALAETSYV | 28 | 270 | A02 | 9 | | 0.0100 | | | | 1072.35 |
| TSYVKVLEY | 3 | 275 | A03/11 | 9 | | | 0.7100 | 0.0100 | | 1072.36 |
| RVRFFFPSLR | 44 | 290 | A03/11 | 10 | | | 0.4300 | 0.0089 | | 1072.37 |
| ALAETSYVK | 32 | 271 | A03/11 | 9 | | | 0.3100 | 0.3600 | | 1072.38 |
| RALAETSYVK | 47 | 270 | A03/11 | 10 | | | 0.1800 | 0.2400 | | 1072.39 |
| DLVQEKYLEY | 14 | 242 | A03 | 10 | | | 0.0320 | 0.0051 | | 1072.40 |
| YVIKVSARVR | 15 | 283 | A03 | 10 | | | 0.0190 | 0.0009 | | 1072.41 |
| LVQEKYLEY | 16 | 243 | A11 | 9 | | | 0.0026 | 0.0340 | | 1072.42 |
| SYVKVLEYVI | 17 | 276 | A24 | 10 | | | | | 0.0360 | 1012.43 |

Immunogenic peptides which were high and intermediate binders were then tested for their capacity to induce an in vitro CTL response.

The assay was carried out as follows:

To identify CTL epitopes, CTL was stimulated by SAC-I activated PBMCs as APC. Cold temperature expression of the MHC in which the β-2-microglobulin is unstable was utilized in addition to acid stripping to generate PBMC APC.

Complete Culture Medium. The tissue culture medium used in this study consisted of RPMI 1640 without Hepes (Biowhittaker) supplemented with 2 mM L-glutamine (Irvine Scientific), 0.5 mM sodium pyruvate (Gibco), 100 U/100 µg/ml penicillin/streptomycin (Irvine), and 5% heat-inactivated Human Serum Type AB (RPMI/5% HS; Gemini Bioproducts). Culture media used in the growth of EBV-transformed lines contained 10% heat-inactivated fetal calf serum (RPMI/10% FCS, Irvine) instead of human serum.

Cytokines. Recombinant human interleukin-2 (rIL-2) and interleukin-4 (rIL-4) were obtained from Sandoz and used at a final concentration of 10 µg/ml and 10 µg/ml, respectively. Human interferon-γ (IFN-γ) and recombinant human Interleukin-7 (rIL-7) were obtained from Genzyme and used at 20 U/ml and 10 ng/ml, respectively.

Peptides. Peptides were synthesized on an automated synthesizer and are described in Table 1. Peptides were routinely diluted in 100% DMSO at 20 mg/ml, aliquoted, and stored at −70° C. Pools of peptides were tested with 2–3 peptides/pool with no more than 5 fold differences in Class I binding (if a pool was not possible for a specific peptide then individual peptides were tested).

Cell Lines. JY, Steinlin, EHM, BVR, and KT3 are homozygous human EBV-transformed B cell lines expressing HLA $A_{2.1}$, $A_1$, $A_3$, $A_{11}$, and $A_{24}$, respectively. They are grown in RPMI/10% FCS. K562, an NK cell sensitive, erythoblastoma line grown in RPMI/10% FCS, was used for reduction of background killing.

Isolation of Peripheral Blood Mononuclear Cells (PBMCs). Whole blood was collected into heparin containing syringes and spun in 50 cc tubes at 1600 RPM (Beckman GS-6KR) for 15 minutes. The plasma layer was then removed and 10 ml of buffy coat was collected with a pipette using a circular motion (an additional 2 ml from the bottom of the tube was included in the 10 ml). The buffy coat was mixed well and diluted with an equal volume of RPMI. The buffy coat (30 ml) was then layered on 20 ml of FICOLL-PAQUE (Pharmacia) and centrifuged at 1850 RPM (400×g) for 20 minutes, 25° C., with the brake off. The interface between the ficoll and the plasma containing the PBMCs was recovered with a transfer pipet (two interfaces per 50 ml tube) and washed three times with 50 ml of RPMI (1700, 1500, and 1300 RPM for 10 minutes). Cells were resuspended in 10–20 ml of culture medium, counted, and adjusted to the appropriate concentration.

Freezing PBMCs. 30 million cells/tube (90% FCS/10% DMSO; Sigma) were inserted into a Nalgene Cryo 1° C. Freezing Container containing Isopropanol (Fisher) and placed at −70° C. from 4 hrs (minimum) to overnight (maximum). The Isopropanol was changed every five times. Tubes were transferred to liquid nitrogen for long term storage. To thaw, PBMCs were continuously shaken in a 37° C. water bath until the last crystal was almost thawed (tubes were not allowed to sit in the water bath or at room temperature for any period of time). Cells were diluted into serum-free RPMI and washed twice.

Induction of Primary CTL Using SAC-I Activated PBMCs as APCs a. Preparation of APCs: PBMCs were purified using the standard FICOLL-PAQUE protocol and resuspended at $1 \times 10^6$/ml in RPMI/5% FCS containing 0.005% PAN-SORBIN cells (SAC-I cells expressing Protein A; Calbiochem), 20 µg/ml IMMUNOBEADS (Rabbit anti-Human IgM; Biorad), and 20 ng/ml of human rIL-4. Two ml of cells per well were plated in a 24-well plate (Falcon, Becton Dickinson) and cultured at 37° C. After 3 days, the medium was removed and the cells were washed three times followed by addition of RPMI/10% HS. The cells were used after culturing for an additional 2 days in RPMI/10% HS.

b. Expression of Empty Class I Molecules on the Surface of APCs and Peptide Loading of APCs 1. Cold Temperature Incubation
   a. Expression of empty MHC in APCs: The APCs were adjusted to a concentration of $2 \times 10^6$/ml in complete culture medium (Section #1) containing 10 ng/ml rIL-4, 20 U/ml human IFN-γ, and 3 µg/ml β2-microglobulin ($\beta_2 m$). The cells were then incubated overnight at 26° C. in the presence of 5% $CO_2$. These cells express only a fraction of Class I molecules in the empty state (~10%).
   b. Peptide loading of APC stimulator cells: Empty Class I expressing APCs were washed 1–2 times with serum free RPMI (+L-glutamine and Hepes)

and resuspended at $1\times10^7$ in serum-free RPMI containing 50 µg/ml total of the peptide pool (i.e., 16.7 µg/ml of each peptide in a pool of three; 25 µg/ml of each peptide in a pool of two; 50 µg/mi of individual peptide), 30 µg/ml DNAse, and 3 µg/ml $\beta_2$m. Following a 4 hour incubation at 20° C., the cells were irradiated at 6100 rads ($5\times10^6$/ml; 25 million cells/tube), washed and adjusted to the appropriate concentration for addition to the induction culture (see below).

2. Acid stripping: This was used as an alternative method for generating empty MHC on the surface of the APCs. The SAC-I activated PBMCs were washed once in cold 0.9% sodium chloride (J. T. Baker) containing 1% BSA. The cells were resuspended at $10^7$/ml in cold citrate-phosphate buffer (0.13M L-ascorbic acid [J. T. Baker], 0.06M sodium phosphate monobasic [Sigma], pH3) containing 1% BSA and 3 µg/ml $\beta_2$m and incubated on ice. After 2 minutes, 5 volumes of cold 0.15M sodium phosphate monobasic buffer, pH7.5, containing 1% BSA, 3 µg/ml $\beta_2$m, and 10 µg/ml peptide [neutralizing buffer #1] was added and the cells centrifuged at 1500 RPM for 5 minutes at 4° C. The cells were resuspended in 1 ml of cold PBS containing 1% BSA, 30 µg/ml DNase, 3 µg/ml $\beta_2$microglobulin, and 50 µg/ml peptide [neutralizing buffer #2] and incubated for 4 hours at 20° C. As above, subsequent to the four hour incubation at 20° C., the cells were irradiated at 6100 rads ($5\times10^6$/ml; 25 million cells/tube), washed, then adjusted to the appropriate concentration for addition to the induction culture (see below).

c. Preparation of the CD4+ depleted PBMC responder cell population (depletion of lymphocyte sub-populations using AIS flasks). AIS MICROCELLECTOR T-150 flasks (specific for the depletion of CD4+ T cells; Menlo Park, Calif.) were primed by adding 25 ml of PBS/1 mM EDTA, swirling for 30 seconds so that all surfaces were moistened, and then incubating with the binding surface down at room temperature for 1 hour. Following this incubation, flasks were shaken vigorously for 30 seconds, washed 1 time with PBS/EDTA, 2 additional times with PBS and then incubated with 25 ml of culture medium for 15 minutes. PBMCs were thawed in serum-free RPMI (+L-glutamine+Hepes) containing 30 µg/ml DNAse, washed once, and incubated for 15 minutes in culture medium. Following aspiration of culture medium from the flasks, up to 180 million PBMCs were added in 25 ml of culture medium containing 30 µg/ml DNAse. After 1 hour at room temperature, the flasks were rocked gently for 10 seconds to resuspend the nonadherent cells. The nonadherent cell suspension containing the CD8+ T cells was collected and the flasks were washed 2 times with PBS. The CD4+ T cell depleted PBMCs were centrifuged and counted for addition to the induction culture. The CD4+ and CD8+ phenotype of the CD4+ depleted cell population was determined by FACS analysis (see below). In general, this technique resulted in a two-fold enrichment for CD8+ T cells with an average of approximately 40–50% CD8+ T cells and 15–20% remaining CD4+ T cells following depletion of CD4+ T cells.

d. Induction of primary CTL. During the 4 hour peptide loading of the stimulator APCs, CD4+ depleted PBMC to be used as the responder population were prepared utilizing AIS flasks for selection of CD8+ T cells through the depletion of CD4+T cells (above). The responder cells were plated at $3\times10^6$/ml in a 1 ml volume (24 well plate) and placed at 37° C. until the peptide loaded stimulator APCs were prepared. The irradiated, peptide loaded APCs were washed 1 time in serum-free RPMI (+L-glutamine and Hepes), adjusted to the appropriate concentration in complete medium, and plated into a 24 well plate at 1 ml/plate: For PBMC, $1\times10^6$ stimulator cells (1 ml volume) were plated into the wells containing the responder cells; For SAC-I activated PBMC and PHA blasts, 1 ml of $3\times10^5$/ml stimulator cells were plated in each well. A final concentration of 10 µg/ml of additional peptide was added in addition to 10 ng/ml final concentration of rIL-7 (2 ml total volume). The cells were cultured for 12 days. (For the "pulse only" induction protocol, the additional 10 µg/ml of soluble peptide was not added to the cultures). On day 12, the cultures were restimulated with peptide pulsed adherent cells and tested for cytolytic activity 7 days later (below).

Protocol for Restimulation of Primary CTL Using Adherent APC. PBMCs were thawed into serum-free RPMI (+L-glutamine and Hepes) containing 30 µg/ml DNAse, washed 2 times, and adjusted to $5\times10^6$/ml in culture medium containing DNAse. PBMCs (25 million cells/tube in 5 ml) were irradiated at 6100R. After 1 wash, the PBMCs were resuspended in culture medium and adjusted to $4\times10^6$/ml. 1 ml of irradiated PBMCs was added per well of a 24-well plate. The PBMC were incubated for 2 hours at 37° C., washed 3 times to remove non-adherent cells, and cultured in medium containing 20 µg/ml total peptide and 3 µg/ml $\beta_2$microglobulin added in a 0.5 ml volume and again incubated for 2 hours at 37° C. The peptide was aspirated and $1.5\times10^6$ responder cells resuspended in culture medium were added in a 1 ml volume. After 2 days, 1 ml of culture medium containing 20 U/ml rIL-2 was added.

FACS Analysis. One million cells/tube were centrifuged, resuspended in 100 µl/tube PBS/0.1% BSA/0.02% sodium azide (Sigma) plus 10 µl/tube directly conjugated antibody (Becton Dickinson), and incubated on ice 15–20 minutes. Cells were then washed 2 times with PBS/0.1% BSA/0.02% sodium azide and resuspended in PBS to analyze on FACScan (Becton Dickinson). When it was not possible to analyze samples within 1–2 days, cells were fixed with PBS containing 1% paraformaldehyde (Fisher) and analyzed within one week.

Cytotoxicity Assays a. Target cell preparation. Approximately 16–20 hours prior to the CTL assay, target cells (Class I matched EBV-transformed lines) were washed once and resuspended in a 10 ml volume at $3\times10^5$/ml in RPMI/5% FCS in the presence or absence of 10 µg/ml total peptide.

b. Labeling of target cells: Target cells were centrifuged and resuspended in 200 µl/tube sodium $^{51}$Cr chromate (NEN), then incubated at 37° C. for 1 hour on a shaker. Targets were washed 3 times (10 ml/wash) with RPMI/10% FCS and resuspended in 10 ml (to determine the efficiency of labelling, 50 µl/target was counted on the MICROMEDIC automatic gamma counter).

c. CTL assay. Target cells were adjusted to $2\times10^5$/ml and 50 µl of the cell culture was added to each well of a U-bottomed 96-well plate (Costar Corp.) for a final concentration of $1\times10^4$/well. K562 cells were washed once, resuspended at $4\times10^6$/ml, and 50 µl/well was added for a final concentration of $2\times10^5$/well (ratio of cold K562 to target was 20:1). Responder cells were washed once, resuspended at $9\times10^6$/ml, and three fold serial dilutions were performed for effector to target ratios of 90:1, 30:1, 10:1, and 3:1. Responder cells were added in a volume of 100 µl in duplicate wells. For spontaneous release, 50 µl/well of labelled target cells, 50 µl/well K562, and 100 µl/well of medium was added. For maximum release, 50 µl/well target, 50 µl/well K562, and 100 µl/well of 0.1% TRITON-X100

(Sigma) was added. Plates were centrifuged for 5 minutes at 1200 RPM. Following a 5 hour incubation at 37° C., plates were centrifuged again for 5 minutes at 1200 RPM, and 100 μl/well of supernatant was collected. Standard gamma counting techniques (Micromedic automatic gamma counter; 0.5 minutes/tube) were used to determine the percent specific lysis according to the formula: % specific lysis=cpm experimental–cpm spontaneous release/cpm maximum release–cpm spontaneous release×100. A CTL assay was considered positive if the lysis by CTL of targets sensitized with a specific peptide at the two highest effector to target (E:T) ratios was 15% greater than lysis of control targets (i.e., target cells without peptide). A cytotoxicity assay was considered borderline if the lysis by CTL of targets sensitized with a specific peptide at the two highest E:T ratios was 6% greater than lysis of control targets. Of the 63 MAGE peptides that bind to the indicated alleles 12 induced primary CTL responses.

Figure 3B:
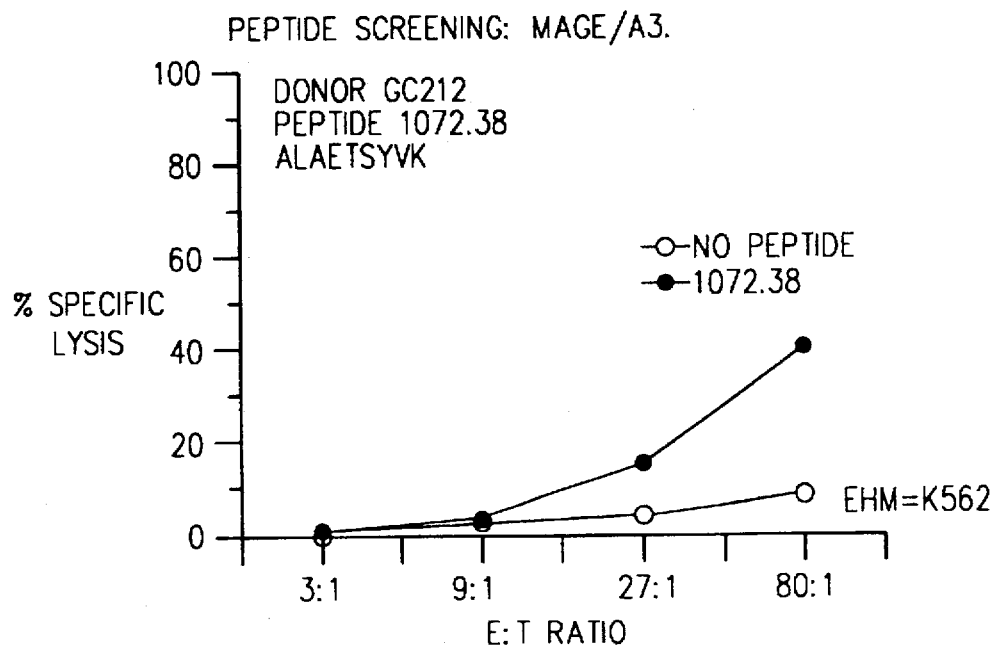

Results of the CTL assays are shown in FIGS. 3A–C.

Although the present invention has been described in some detail by way of illustration and example for purposes of clarity and understanding, it will be apparent that certain changes and modifications may be practiced within the scope of the appended claims.

---

What is claimed:

1. An isolated cDNA encoding a cytotoxic T lymphocyte immunogenic peptide of at least nine contiguous amino acids selected from the 58 amino acids of Sequence I.D. No. 1.

2. A vector comprising cDNA encoding cytotoxic T lymphocyte immunogenic peptide of at least nine contiguous amino acids selected from the 58 amino acids of Sequence I.D. No. 1.

3. A host cell transformed with the vector of claim 2.

* * * * *